(12) United States Patent
Yusuf et al.

(10) Patent No.: US 10,267,774 B2
(45) Date of Patent: Apr. 23, 2019

(54) EXTERNAL NOISEMAKER FOR PIPE SYSTEMS

(71) Applicant: Mueller International, LLC, Atlanta, GA (US)

(72) Inventors: Shabbir Yusuf, Mississauga (CA); Werner Guenther Richarz, Thornhill (CA); Valentin Mircea Burtea, Toronto (CA); Filip Stefanovic, Toronto (CA)

(73) Assignee: Mueller International, LLC, Atlanta, GA (US)

( * ) Notice: Subject to any disclaimer, the term of this patent is extended or adjusted under 35 U.S.C. 154(b) by 221 days.

(21) Appl. No.: 15/056,403

(22) Filed: Feb. 29, 2016

(65) Prior Publication Data

US 2017/0248555 A1 Aug. 31, 2017

(51) Int. Cl.
  *G10K 9/12* (2006.01)
  *G01N 29/07* (2006.01)
  *G01N 29/34* (2006.01)

(52) U.S. Cl.
  CPC .............. *G01N 29/34* (2013.01); *G01N 29/07* (2013.01); *G10K 9/12* (2013.01); *G01N 2291/0289* (2013.01); *G01N 2291/02854* (2013.01)

(58) Field of Classification Search
  CPC .................. G01N 29/34; G01N 29/07; G01N 2291/0289; G01N 2291/02854; G10K 9/12
  USPC .......................................................... 73/662
  See application file for complete search history.

(56) References Cited

U.S. PATENT DOCUMENTS

| 3,011,754 | A |   | 12/1961 | Ander |
|---|---|---|---|---|
| 3,216,244 | A |   | 11/1965 | Borchers |
| 3,283,833 | A | * | 11/1966 | Bodine, Jr. ............... E21B 7/24 |
|   |   |   |   | 175/56 |
| 4,194,246 | A | * | 3/1980 | Crist ......................... B01J 7/02 |
|   |   |   |   | 367/1 |
| 4,929,898 | A |   | 5/1990 | Spies |
| 5,031,446 | A |   | 7/1991 | Saito et al. |
| 5,037,327 | A | * | 8/1991 | Van Woensel ....... H01R 12/727 |
|   |   |   |   | 439/571 |
| 5,526,689 | A |   | 6/1996 | Coulter et al. |
| 5,836,787 | A | * | 11/1998 | Kodama ............ H01R 13/6215 |
|   |   |   |   | 439/567 |

(Continued)

FOREIGN PATENT DOCUMENTS

| CN | 202867884 | 4/2013 |
|---|---|---|
| CN | 2003404430 | 1/2014 |

(Continued)

OTHER PUBLICATIONS

Yusuf, Shabbir; International Search Report and Written Opinion for serial No. PCT/US2016/036856, filed Jun. 10, 2016, dated Sep. 9, 2016, 10 pgs.

(Continued)

*Primary Examiner* — Jacques M Saint Surin
(74) *Attorney, Agent, or Firm* — Taylor English Duma LLP

(57) ABSTRACT

A noisemaker system includes: a node of an infrastructure system; and a noisemaker including a vibrating plate, the vibrating plate including a top surface and a bottom surface, the bottom surface of the vibrating plate in contact with an exterior surface of the node, and an actuator configured to engage the top surface of the vibrating plate and generate an acoustic signal.

17 Claims, 6 Drawing Sheets

(56) References Cited

U.S. PATENT DOCUMENTS

| | | | |
|---|---|---|---|
| 6,289,723 | B1 | 9/2001 | Leon |
| 6,453,247 | B1 | 9/2002 | Hunaidi |
| 6,556,924 | B1 | 4/2003 | Kariyawasam |
| 6,561,032 | B1 | 5/2003 | Hunaidi |
| 7,266,992 | B2 | 9/2007 | Shamout et al. |
| 7,283,913 | B2 | 10/2007 | Garnaes |
| 7,328,618 | B2 | 2/2008 | Hunaidi |
| 7,475,596 | B2 | 1/2009 | Hunaidi |
| 7,810,378 | B2 | 10/2010 | Hunaidi |
| 7,830,273 | B2 | 11/2010 | Twitchell, Jr. |
| 7,940,189 | B2 | 5/2011 | Brown |
| 8,296,083 | B2 | 10/2012 | Martin |
| 8,816,866 | B2 | 8/2014 | Day |
| 8,966,979 | B2 | 3/2015 | Amundsen |
| 9,291,520 | B2 * | 3/2016 | Fleury, Jr. .............. G01M 3/00 |
| 9,541,432 | B2 | 1/2017 | Kertesz |
| 9,651,445 | B2 * | 5/2017 | McIntyre ............. G01M 3/005 |
| 9,670,650 | B2 * | 6/2017 | Pinney .................... E03B 7/072 |
| 9,799,204 | B2 * | 10/2017 | Hyland ............... G08B 25/006 |
| 9,835,592 | B2 | 12/2017 | Yusuf et al. |
| 9,861,848 | B2 * | 1/2018 | Hyland ................. A62C 37/50 |
| 10,067,092 | B2 | 9/2018 | Burtea et al. |
| 2001/0032064 | A1 | 10/2001 | Araki et al. |
| 2003/0033870 | A1 | 2/2003 | Shah et al. |
| 2003/0033879 | A1 | 2/2003 | Adewumi |
| 2004/0169108 | A1 * | 9/2004 | Terpay .................. B64C 27/615 244/17.11 |
| 2005/0210960 | A1 | 9/2005 | Shamout et al. |
| 2006/0283251 | A1 | 12/2006 | Hunaidi |
| 2007/0041333 | A1 | 2/2007 | Twitchell |
| 2009/0250125 | A1 | 10/2009 | Howitt |
| 2010/0175477 | A1 * | 7/2010 | Kasai ................... H04R 19/005 73/649 |
| 2012/0125111 | A1 | 5/2012 | Groos et al. |
| 2012/0167688 | A1 | 7/2012 | Minachi et al. |
| 2013/0025375 | A1 | 1/2013 | Goldner et al. |
| 2013/0036796 | A1 | 2/2013 | Fleury |
| 2013/0058819 | A1 * | 3/2013 | Kodama ............... F04B 43/043 417/479 |
| 2013/0211797 | A1 | 8/2013 | Scolnicov |
| 2013/0240093 | A1 | 9/2013 | Okada |
| 2015/0247777 | A1 | 9/2015 | Kondou |
| 2016/0208952 | A1 | 7/2016 | Howitt |
| 2016/0223120 | A1 | 8/2016 | Gagliardo |
| 2016/0252422 | A1 | 9/2016 | Howitt |
| 2016/0290974 | A1 | 10/2016 | Coleman |
| 2017/0176395 | A1 * | 6/2017 | Burtea .................... G01N 29/07 |
| 2018/0340912 | A1 | 11/2018 | Burtea et al. |

FOREIGN PATENT DOCUMENTS

| | | |
|---|---|---|
| FR | 2754898 | 4/1998 |
| JP | 2002236115 | 8/2002 |
| WO | 2010020817 | 2/2010 |
| WO | 2015073313 | 5/2015 |
| WO | 2016160267 | 10/2016 |

OTHER PUBLICATIONS

Bak, et al; Article entitled: "Acoustic attenuation, phase and group velocities in liquid-filled pipes: Theory, experiment, and examples of water and mercury", J. Acoust. Soc. Am. 128(5), Nov. 2010, 15 pgs.

Yusuf, Shabbir; Notice of Allowance for U.S. Appl. No. 14/740,902, filed Jun. 16, 2015, dated Aug. 30, 2017, 5 pgs.

Yusuf, Shabbir; Supplemental Notice of Allowability for U.S. Appl. No. 14/740,902, filed Jun. 16, 2015, dated Sep. 15, 2017, 4 pgs.

Burtea, Valentin Mircea; Non-Final Office Action for U.S. Appl. No. 14/974,351, filed Dec. 18, 2015, dated Nov. 3, 2017, 33 pgs.

Coleman, Matthew Simon; International Preliminary Report on Patentability for PCT Application No. PCT/US2016/020889, filed Mar. 4, 2016, dated Oct. 12, 2017, 13 pgs.

Coleman, Matthew, Simon; International Search Report and Written Opinion for PCT Application No. PCT/US2016/020889, filed Mar. 4, 2016, dated Jun. 6, 2016, 14 pgs.

De Silva et al., Condition Assessment and Probabilistic Analysis to Estimate Failure Rates in Buried Pipelines, Thermo Scientific, In: Proceedings of ASTT 5th Conference. Aug. 2002 {Aug. 2002). Retrieved from <https://www.researchgate.net/profile/Magnus_Moglia/publication/236834972_Condition_Assessment_and_Probabilistic_Analaysis_to_Estimate_Failure_Rates_in_Buried_Pipelines/links/00b7d51945e4007c48000000/pdf>, 21 pgs.

Sheppard et al., Cast Iron Fitness for Purpose (FFP)—Final Report, Macaw Engineering, Ltd., Jun. 3, 2015, Retrieved from <http://www.smartemetworks.org/Files/Cast_Iron_Fitness_For_Purpose_{CIFFP)_151214123856.pdf>, 91 pgs.

Yusuf, Shabbir; PCT Application entitled: A Determination of Tuberculation in a Fluid Distribution System, having serial No. PCT/US2016/036856, filed Jun. 10, 2016, 27 pgs.

Coleman, Matthew Simon; PCT Application entitled: Determination of Pipe Wall Failure Based on Minimum Pipe Wall Thickness having serial No. PCT/US16/20889, filed Mar. 4, 2016, 35 pgs.

Coleman, Matthew Simon; U.S. Patent Application entitled: Determination of Pipe Wall Failure Based on Minimum Pipe Wall Thickness, having U.S. Appl. No. 14/674,851, filed Mar. 31, 2015, 31 pgs.

Hay, Lindsay; "The Influence of Soil Properties on the Performance of Underground Pipelines", Department of Soil Science, The Faculty of Agriculture, The University of Sydney, Aug. 1984, 243 pgs.

Makar, et al.; "Failure Modes and Mechanisms in Gray Cast Iron Pipe", National Research Council Canada, Copyright 2000, 11 pgs.

Muster, et al.; "Life Expectancy of Cement Mortar Linings in Cast and Ductile Iron Pipes", Water Research Foundation, Copyright 2011, 192 pgs.

Rajani, et al.; "Impact of Soil Properties on pipe corrosion: re-examination of traditional conventions", National Research Council Canada, Sep. 2010, 17 pgs.

Rajani, et al.; "Investigation of Grey Cast Iron Water Mains to Develop a Methodology for Estimating Service Life", AWWA Research Foundation, Copyright 2000, 294 pgs.

Yusuf, Shabbir; U.S. Patent Application entitled: Determination of Tuberculation in a Fluid Distribution System having U.S. Appl. No. 14/740,902, filed Jun. 16, 2015, 29 pgs.

Burtea, Valentin Mircea; U.S. Patent Application entitled: Noise-maker for Pipe Systems, having U.S. Appl. No. 14/974,351, filed Dec. 18, 2015, 25 pgs.

Sewerin; Operating Instructions for Combiphon, dated Dec. 10, 2011; 32 pgs.

Coleman, Matthew Simon; Non-Final Office Action for U.S. Appl. No. 14/674,851, filed Mar. 31, 2015, dated Jun. 16, 2017, 50 pgs.

Yusuf, Shabbir; Non-Final Office Action for U.S. Appl. No. 14/740,902, filed Jun. 16, 2015, dated Apr. 27, 2017, 22 pgs.

Coleman, Matthew Simon; Final Office Action for U.S. Appl. No. 14/674,851, filed Mar. 31, 2015, dated Dec. 15, 2017, 38 pgs.

Yusuf, Shabbir; Issue Notification for US. Appl. No. 14/740,902, filed Jun. 16, 2015, dated Nov. 15, 2017, 1 pg.

Yusuf, Shabbir; International Preliminary Report on Patentability for serial No. PCT/US2016/036856, filed Jun. 10, 2016, dated Dec. 28, 2017, 9 pgs.

Coleman, Matthew Simon; Final Office Action for U.S. Appl. No. 14/674,851, filed Mar. 31, 2015, dated May 21, 2018, 36 pgs.

Burtea, Valentin Mircea; Notice of Allowance for U.S. Appl. No. 14/974,351, filed Dec. 18, 2015, dated May 10, 2018, 10 pgs.

Burtea, Valentin Mircea; Supplemental Notice of Allowance for U.S. Appl. No. 14/974,351, filed Dec. 18, 2015, dated May 24, 2018, 6 pgs.

Burtea, Valentin Mircea; Issue Notification for U.S. Appl. No. 14/974,351, filed Dec. 18, 2015, dated Aug. 21, 2018, 1 pg.

Burtea, Valentin Mircea; Supplemental Notice of Allowance for U.S. Appl. No. 14/974,351, filed Dec. 18, 2015, dated Aug. 10, 2018, 6 pgs.

Baik, et al.; Article entitled: "Acoustic attenuation, phase and group velocities in liquid-filled pipes . . . ", 2010 Acoustical Society of America, published Nov. 2010, 15 pgs.

(56) References Cited

OTHER PUBLICATIONS

Yusuf, Shabbir; Written Opinion for Singapore patent application No. 11201710434V, filed Jun. 10, 2016, dated May 31, 2018, 6 pgs.
Price, John; Article entitled: "Acoustic Waveguides", Jan. 22, 2008 (Jan. 22, 2008), XP055522269, Retrieved from the inventor: http://spot.colorado.edu/~pricej/downloads/AcousticWaveguides.pdf; retrieved on Nov. 8, 2018, 32 pgs.
Yusuf, Shabbir; Extended European Search Report for serial No. 16812182.0, filed Jun. 10, 2016, dated Nov. 21, 2018, 22 pgs.

\* cited by examiner

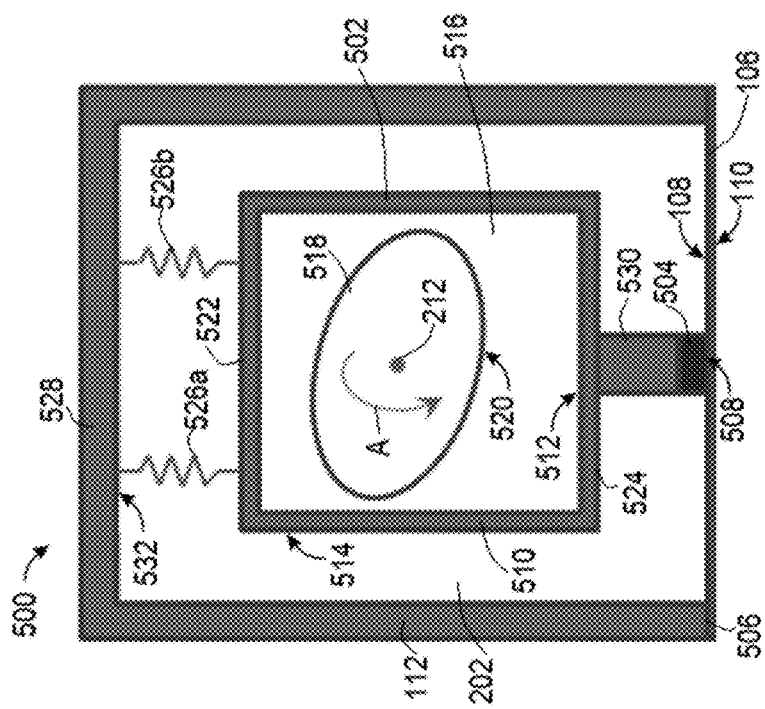
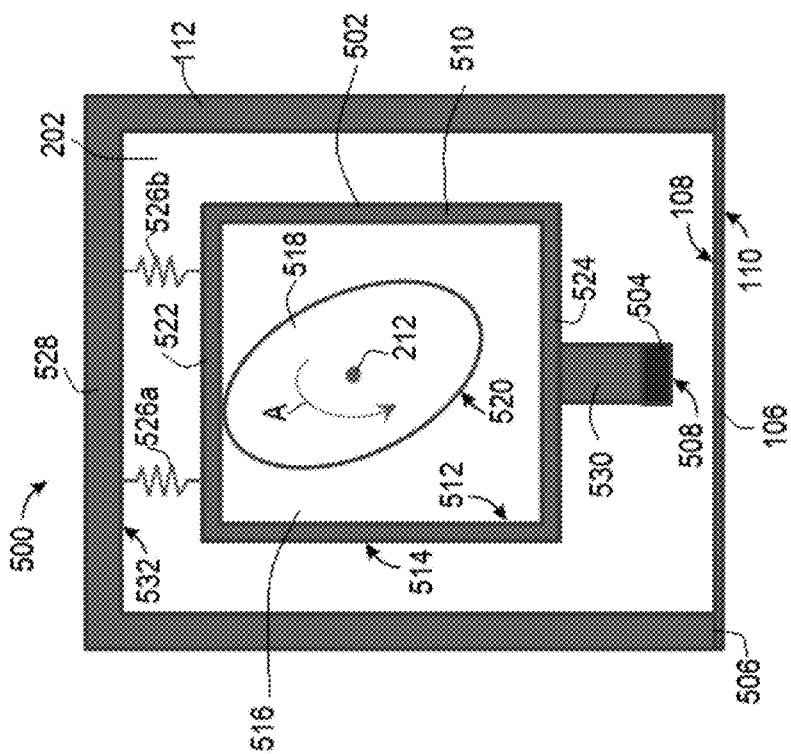

EXTERNAL NOISEMAKER FOR PIPE SYSTEMS

BACKGROUND

Field

This application relates to noisemakers, and more particularly, this disclosure relates to devices which generate noise in fluid pipe systems.

Background Technology

As infrastructure pipe systems, such as those in the water, wastewater, oil, or gas industries, reach the end of their service lives, they tend to leak more, have leaks that can be more difficult to find, and have higher risks of catastrophic failure. For example, pipes in the system may lose metal resulting in a reduction in pipe wall thickness, typically as a result of internal and external corrosion. Sustained wall thickness loss eventually causes the pipes to fail. Main breaks, as well as pipe age and material, have historically been the key determinants for selecting pipes to replace or rehabilitate. However, these factors may not be indicative of the current or even future condition of the pipeline because pipes may decay at different rates, even if pipes can be the same age and close in physical proximity. Finding these weakened pipes, especially along long lines of underground or otherwise inaccessible pipes, therefore assists in protecting pipe system integrity.

SUMMARY

Described herein can be a noisemaker system and a method of generating sound in an infrastructure system. The noisemaker system can be configured for use with the infrastructure system. In one aspect, the noisemaker system can comprise a node of an infrastructure system. Further, the noisemaker system can comprise a noisemaker. The noisemaker can comprise a vibrating plate, which can comprise a top surface and a bottom surface. The bottom surface of the vibrating plate can be in contact with an exterior surface of the node. The noisemaker can further comprise an actuator, which can be configured to engage the top surface of the vibrating plate and generate an acoustic signal.

In another aspect, a noisemaker can comprise a noisemaker housing. The noisemaker housing can define a noisemaker cavity and a housing opening. The vibrating plate can be secured to the noisemaker housing and positioned proximate to the housing opening.

In a further aspect, the method of generating sound in the infrastructure system can comprise: placing a bottom surface of the vibrating plate of the noisemaker in contact with an exterior surface of a pipe element of the infrastructure system; and generating an acoustic signal by contacting the actuator of the noisemaker with the top surface of the vibrating plate.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

FIG. 5A is a block diagram of a noisemaker comprising an actuator and a vibrating plate with the actuator in a disengaged position in accordance with one aspect of the current disclosure.

FIG. 5B is a block diagram of the noisemaker of FIG. 5A with the actuator and the vibrating plate in an engaged position according to aspects of the current disclosure.

DETAILED DESCRIPTION

Figure 1:
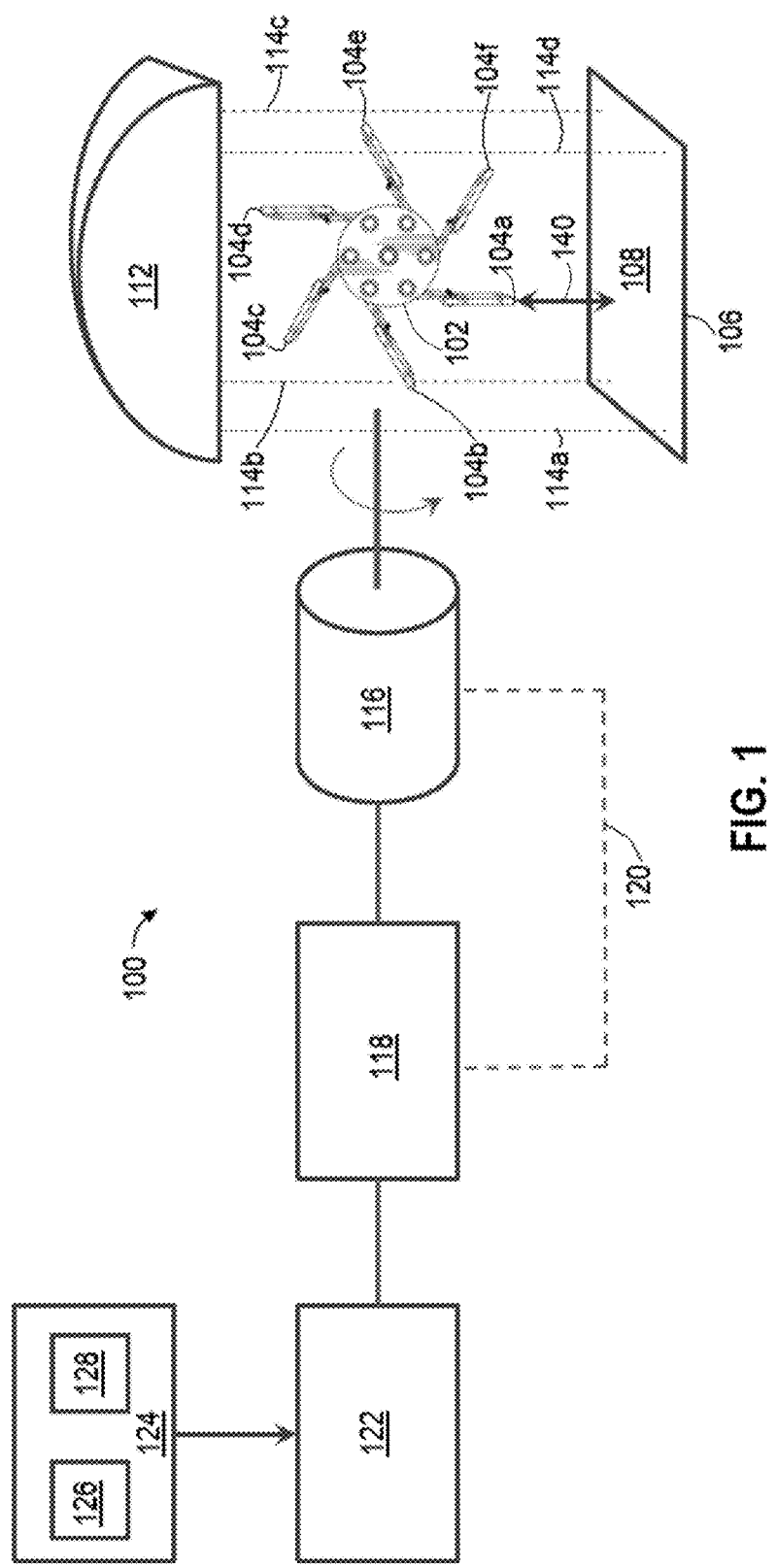
FIG. 1 is a block diagram of a noisemaker showing an actuator and a vibrating plate in accordance with one aspect of the current disclosure.

The present invention can be understood more readily by reference to the following detailed description, examples, drawings, and claims, and their previous and following description. However, before the present devices, systems, and/or methods can be disclosed and described, it can be to be understood that this invention can be not limited to the specific devices, systems, and/or methods disclosed unless otherwise specified, and, as such, can, of course, vary. It can be also to be understood that the terminology used herein can be for the purpose of describing particular aspects only and can be not intended to be limiting.

The following description of the invention can be provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention can be possible and can even be desirable in certain circumstances and can be a part of the present invention. Thus, the following description can be provided as illustrative of the principles of the present invention and not in limitation thereof.

As used throughout, the singular forms "a," "an" and "the" include plural referents unless the context clearly dictates otherwise. Thus, for example, reference to "a band" can include two or more such bands unless the context indicates otherwise.

Ranges can be expressed herein as from "about" one particular value, and/or to "about" another particular value. When such a range can be expressed, another aspect includes from the one particular value and/or to the other particular value. Similarly, when values can be expressed as approximations, by use of the antecedent "about," it will be understood that the particular value forms another aspect. It will be further understood that the endpoints of each of the ranges can be significant both in relation to the other endpoint, and independently of the other endpoint.

As used herein, the terms "optional" or "optionally" mean that the subsequently described event or circumstance can or can not occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "can," unless specifically stated otherwise, or otherwise understood within the context as used, can be generally intended to convey that certain aspects include, while other aspects do not include, certain features, elements and/or steps. Thus, such conditional language can be not generally intended to imply that features, elements and/or steps can be in any way required for one or more particular aspects or that one or more particular aspects necessarily include logic for deciding, with or without user input or prompting, whether these features, elements and/or steps can be included or can be to be performed in any particular embodiment. Directional references such as "up," "down," "top," "left," "right," "front," "back," and "corners," among others can be intended to refer to the orientation as illustrated and described in the figure (or figures) to which the components and directions can be referencing.

In one aspect, disclosed can be a noisemaker and associated methods, systems, devices, and various apparatus. The noisemaker can comprise an actuator and a vibrating plate. It would be understood by one of skill in the art that the disclosed noisemaker can be described in but a few exemplary aspects among many.

Noisemakers can be devices designed to generate noise in infrastructure piping systems, such as water pipes. In various aspects, an infrastructure system can be a water infrastructure system. The infrastructure system conventionally can comprise various nodes such as pipes, hydrants, exposed pipes, meters, pumps, valves, storage tanks, and various other access or connection points. For example and without limitation, a node of the infrastructure system can be a fire hydrant. In various aspects, the generated noise can be used to measure the velocity of sound in the pipe, which can be utilized for pipe wall assessment.

In various aspects, the velocity of sound in the pipe can be indicative of the condition of the pipeline. For example and without limitation an average minimum pipe wall thickness can be determined from the average propagation velocity of sound in the pipe. The propagation velocity of noise can depend on parameters such as the internal diameter and circumferential thickness profile of the pipe, density and bulk modulus of elasticity of the fluid in the pipe, and Young's modulus of elasticity and Poisson's ratio of the pipe wall material. In various aspects, the propagation velocity, which can be the average propagation velocity, can be determined by measuring the time delay between acoustic signals measured at two points on a pipe that can be a known distance apart, such as at a control valve, fire hydrant, or other point on the pipe, using devices such as hydrophones or vibration sensors. The generated noise can also be utilized to locate a pipe with various listening or sound-measuring equipment. The frequency and regularity of the noise can also be adjusted based on the different parameters of the system to obtain better readings.

As described below, a noisemaker can be a sound source and generally can comprise a vibrating plate and an actuator. The actuator can be configured to engage the vibrating plate and generate an acoustic signal. When the noisemaker can be in contact with a node of an infrastructure system, such as a pipe element or a fire hydrant of a water system, the acoustic signal generated by the actuator can be transferred to the node and can propagate through the infrastructure system.

A block diagram of a noisemaker 100 can be disclosed and described in FIG. 1. In one aspect, the noisemaker 100 can comprise an actuator 102 and a vibrating plate 106. As described in greater detail below, the actuator 102 can be configured to engage the vibrating plate 106 to generate an acoustic signal. The noisemaker 100 can be utilized with infrastructure piping systems. For example and without limitation, the noisemaker can be utilized with water distribution piping systems, gas distribution, pressure distribution piping systems, or various other types of piping systems. Optionally, the noisemaker 100 can be used at various nodes within the system. For example and without limitation, the noisemaker 100 can be utilized at control valves, pipe elements, or fire hydrants in water distribution systems. In various aspects where the node can be a fire hydrant, the fire hydrant can be a dry barrel hydrant and the noisemaker 100 can contact an exterior surface of the fire hydrant, such as an exterior surface of a nozzle of the fire hydrant. In various other aspects, the node can be a wet barrel hydrant, or the node can be various other access points of a pipe network such as various valves, pipe elements, hydrants, or other access points.

In one aspect, the actuator 102 can comprise tapping tips 104$a,b,c,d,e,f$, which can be configured to engage the vibrating plate 106. In one non-limiting example, the actuator 102 can comprise the six tapping tips 104$a,b,c,d,e,f$. However, the number of tapping tips 104 should not be considered limiting on the current disclosure as it can be also contemplated that the actuator 102 can comprise any number of tapping tips 104. In various aspects, the tapping tips 104 can be constructed from various materials depending on the node (e.g. pipe) material, type of signal that the operator wants to generate, and the size of the pipe in which the acoustic signal is to be generated. For example and without limitation, in these aspects a tapping tip 104 configured to generate the acoustic signal in a small diameter metallic pipe can be constructed from a relatively harder material compared to a material used to construct a tapping tip 104 configured to generate the acoustic signal in a plastic pipe. For example and without limitation, the tapping tip 104 can be constructed from aluminum, various rubbers, steel reinforced rubber, steel wire, and various other materials that can be utilized to generate an acoustic signal.

Figure 2:
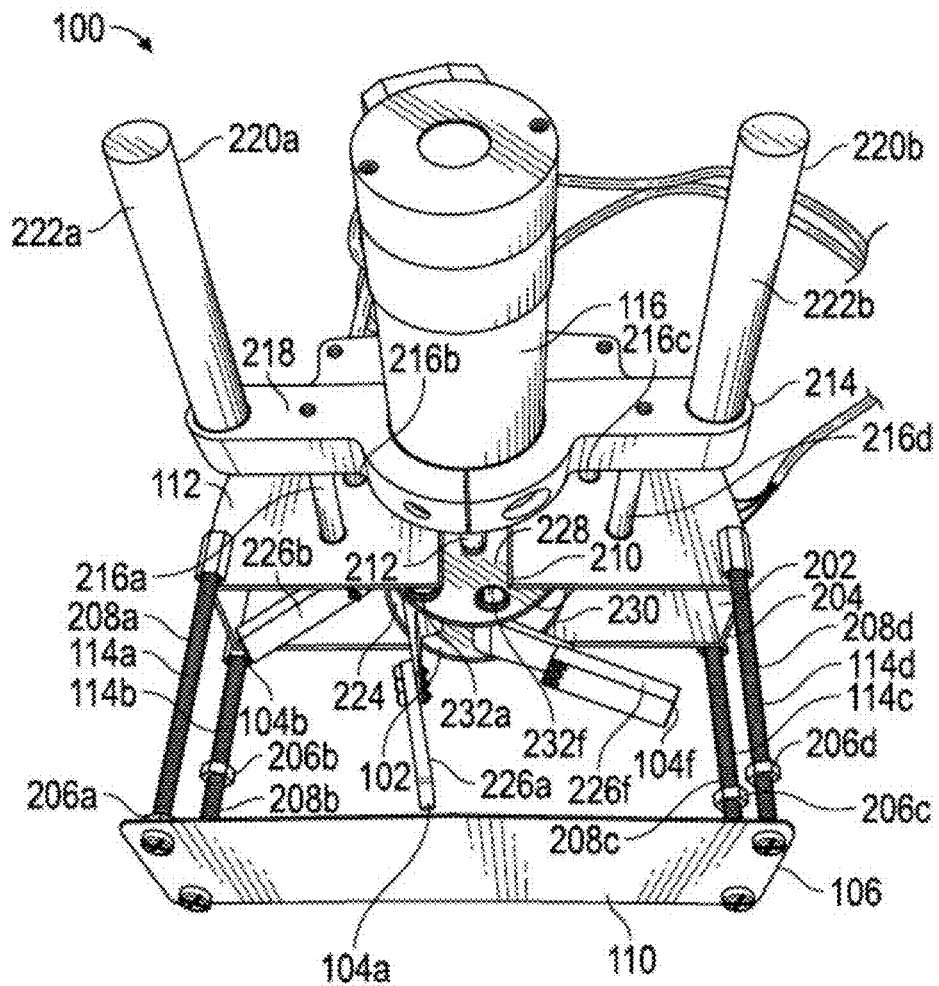
FIG. 2 is a perspective view of a noisemaker comprising an actuator and a vibrating plate in accordance with one aspect of the current disclosure.

In another aspect, the vibrating plate 106 can comprise a top surface 108 and a bottom surface 110 (shown in FIG. 2). In one aspect, the vibrating plate 106 can be constructed from various materials depending on the node material, type of signal that the operator wants to generate, and the size of the pipe in which the acoustic signal is to be generated. In this aspect, the vibrating plate 106 can be constructed from various materials that can be similar to the material that can be used for the tapping tip 104 or different from the material that can be used for the tapping tip 104. In various aspects, the bottom surface 110 can be placed in contact with an exterior surface of the node of the infrastructure system. Optionally, the tapping tips 104 of the actuator 102 can be configured to engage the top surface 108 of the vibrating plate 106 by rotation of the actuator 102 and generate the acoustic signal. The vibrating plate 106 enables the actuator 102 to indirectly impact the node while protecting the node from damage, such as paint damage, pipe wall damage, and various other types of damage that may otherwise result if the actuator 102 were to directly engage the node. In another aspect, the vibrating plate 106 can set a specific distance or set point at which the actuator 102 strikes the vibrating plate 106, which can allow for control over the frequency and amplitude of the noise generated.

In yet another aspect, vibrating plate 106 can be positioned at an adjustable distance 140 from the actuator 102. In one aspect, it can be contemplated that an operator can adjust the distance at which the vibrating plate 106 can be positioned from the tapping tips 104 of the actuator 102 to adjust the magnitude of the impact force that results from the actuator 102 engaging the vibrating plate 106. In these aspects, the adjustable impact force can be utilized by the operator to generate a desired acoustic signal with the noisemaker 100. In a further aspect, it can be contemplated that adjusting the position of the vibrating plate 106 relative to the tapping tips 104 also can adjust a duration of the impact of the actuator 102 with the vibrating plate 106. For example and without limitation, the vibrating plate 106 positioned relatively close to the actuator 102, such as at a minimal distance between the top surface 108 of the vibrating plate 106 and the actuator 102, can comprise a longer impact duration between one of the tapping tips 104 and the vibrating plate 106 relative to an impact duration when the vibrating plate 106 can be positioned relatively distal from the actuator 102, such as at a maximum distance between the top surface 108 of the vibrating plate 106 and the actuator 102.

In one aspect, the noisemaker 100 can comprise a noisemaker housing 112. The noisemaker housing 112 can define a noisemaker cavity (not shown in FIG. 1). In one preferred aspect, it can be contemplated that the actuator 102 can be positioned at least partially within the noisemaker cavity; however, it can be contemplated that the actuator can be fully within the noisemaker cavity. Optionally, the vibrating plate 106 can be secured to the noisemaker housing 112 through connectors 114*a,b,c,d*. The number of connectors 114 should not be considered limiting on the current disclosure as it can be also contemplated that the vibrating plate 106 can be connected to the noisemaker housing 112 through at least one connector 114. Optionally, it can be contemplated that the connectors 114 can be adjustable connectors that can be configured to adjustably position the vibrating plate 106 at the adjustable distance 140 from the actuator 102. For example and without limitation, it can be contemplated that the connectors 114 can be selected from the group including, but not limited to, nuts and bolts, screws, pins, rods, telescoping rods, and various other types of connectors. In a further aspect, it can be also contemplated that the connectors 114 can be secured to at least one of the vibrating plate 106 and the noisemaker housing 112 via securing mechanisms such as, for example and without limitation, threading, welding, adhesives, and various other mechanisms.

As shown in FIG. 1, in a further aspect the noisemaker 100 can comprise a motor 116. The motor 116 can be coupled to the actuator 102 and can be configured to drive, and thereby rotate, the actuator 102 to engage the top surface 108 of the vibrating plate 106. In one aspect, a frequency at which the actuator 102 engages the vibrating plate 106 can be proportional to a frequency at which the motor 116 drives the actuator 102. In one non-limiting example, the motor 116 can be configured to rotate the actuator 102 through a gear (not shown), and the frequency at which the motor 116 rotates the gear can be proportional to the frequency at which the tapping tips 104 of the actuator 102 engage the top surface 108 of the vibrating plate 106. The actuator 102 can be utilized to produce a brushing contact with the top surface 108 of the vibrating plate 106, as described in greater detail below.

In another aspect, the noisemaker 100 can comprise a motor control 118 communicatively coupled to the motor 116. The motor control 118 can be a frequency control and can be configured to control the frequency at which the motor 116 drives the actuator 102. The motor control 118 can receive sensor feedback 120 from the motor 116. In one aspect, the motor control 118 can utilize the sensor feedback 120 to control the motor 116 such that the motor 116 drives the actuator 102 at a desired constant frequency. In a further aspect, the motor control 118 can be configured to cause the motor 116 to drive the actuator 102 at a predetermined frequency, which, as described previously, can be proportional to a frequency at which the actuator 102 engages the vibrating plate 106. In one non-limiting example, the motor 116 can be configured to rotate the actuator 102 and the motor control 118 can be configured to cause the motor 116 to rotate the actuator 102 at a predetermined rotational speed.

As shown in FIG. 1, the noisemaker 100 can comprise an excitation control 122. The excitation control 122 can be configured to control an excitation pattern of the acoustic signal generated by the actuator 102. It can be contemplated that the excitation pattern can be selected from the group including, but not limited to, frequency sweeps, white noise, multiple tones, impulses, and various other types of excitation patterns. Control of the excitation pattern of the acoustic signal can be described in greater detail below.

Referring to FIG. 1, in one aspect, the noisemaker 100 can comprise a user interface 124. The user interface 124 can be communicatively coupled to the excitation control 122. In another aspect, the user interface 124 can also be communicatively coupled to the motor control 118. It can be contemplated that the operator can utilize the user interface 124 to input or otherwise control various aspects of the noisemaker 100, such as the excitation control 122 and the motor control 118. As one non-limiting example, the operator can use the user interface 124 to select an excitation sequence of the excitation control 122 for the actuator 102. In one aspect, the user interface 124 may include display technology 126, which can be an LCD display or various other types of display technologies. In another aspect, the user interface 124 can comprise one or more control buttons 128, which can be utilized to input or otherwise control various aspects of the noisemaker 100. In this aspect, the control button 128 can be an emergency stop switch, that, when activated, stops the motor 116 from driving the actuator 102.

Referring to FIG. 2, the noisemaker housing 112 defines a noisemaker cavity 202 having a noisemaker cavity opening 204. As described previously, the actuator 102 can be positioned at least partially within the noisemaker cavity 202 and the vibrating plate 106 can be offset from the actuator 102 at the adjustable distance 140. As shown in FIG. 2, the noisemaker housing 112 can define a slot 210 dimensioned to accept a drive shaft 212 through the slot 210. The drive shaft 212 can mechanically couple the actuator 102 with the motor 116. In one aspect, the drive shaft 212 can be a rotating shaft that can be configured to rotate the actuator 102. As previously described, the motor 116 can be communicatively coupled to the motor control 118 and the excitation control 122 in various aspects to control the motor 116 driving the actuator 102.

In one aspect, the actuator 102 can comprise a hub 224. Optionally, a plurality of flaps 226a,b,c,d,e,f (flaps 226c,d,e shown in FIG. 3) connected to the hub 224. As shown in FIG. 2, the flaps 226a,b,c,d,e,f extend outwards from the hub 224. In a further aspect, portions of the actuator 102, such as a portion of at least one of the flaps 226 can extend outwards from the noisemaker cavity 202 when the actuator can be positioned at least partially within the noisemaker cavity 202. It will be appreciated that the number of flaps 226 should not be considered limiting on the current disclosure as it can be also contemplated that the actuator 102 includes any number of flaps 226. The hub 224 can be rotated via the motor 116 and the drive shaft 212. In this aspect, the hub 224 can rotate the flaps 226. An angle θ (shown in FIG. 3) at which each of the flaps 226a,b,c,d,e,f extends from the hub 224 with respect to a radial direction 302 (shown in FIG. 3) can be adjusted. In one preferred aspect, all of the flaps 226a,b,c,d,e,f extend from the hub 224 at the same angle θ; however, it can be contemplated that each of the flaps 226a,b,c,d,e,f can extend from the hub 224 at a different angle compared to the other flaps 226a,b,c,d,e,f. In another aspect, the actuator 102 can comprise solid pieces of rubber, metal brushes comprising a plurality of strands, and various other structures for engaging the vibrating plate 106 that can be connected to the hub 224.

In yet another aspect, the hub 224 can comprise a top hub plate 228 and a bottom hub plate 230. The flaps 226a,b,c,d,e,f can be secured to the hub 224 between the plates 228,230 via flap connectors 232a,b,c,d,e,f (connectors 232b,c,d,e shown in FIG. 3). It can be contemplated that the flap connectors 232 can be selected from the group including, but not limited to, nuts and bolts, screws, pins, and various other types of flap connectors suitable for securing the flaps 226 to the hub 224.

As shown in FIG. 2, in one aspect, the connectors 114a,b,c,d can be nuts 206a,b,c,d and bolts 208a,b,c,d for securing the vibrating plate 106 to the housing 112. In this aspect, the vibrating plate 106 can define a number of flap securing bores (not shown) extending through the vibrating plate 106 from the bottom surface 110 to the top surface 108. It can be contemplated that the number of securing bores can correspond with the number of connectors 114. The bolts 208a,b,c,d of the connectors 114a,b,c,d can be positioned through the securing bores, respectively, such that the vibrating plate 106 can be mounted on the bolts 208a,b,c,d of the connectors 114a,b,c,d. The bolts 208a,b,c,d can be secured to the noisemaker housing 112 via securing mechanisms such as, for example and without limitation, threading, welding, adhesives, and various other mechanisms. In one aspect, the nuts 206a,b,c,d can be utilized to adjustably position the vibrating plate 106 on the bolts 208a,b,c,d, respectively, to adjustably position the vibrating plate 106 relative to the actuator 102. In this aspect, the distance between the vibrating plate 106 and the actuator 102 can be adjustable. The placement of the nuts 206 in FIG. 2 can be shown in untightened positions, but to set the adjustable distance 140, the nuts 206 can be tightened against the vibrating plate 106.

In another aspect, the noisemaker 100 can comprise a handle assembly 214. The handle assembly 214 can comprise a body 218 and handles 220a,b. Each handle 220a,b can define an outer surface 222a,b, respectively, which the operator may grip or hold. The handles 220a,b can be utilized by the operator to hold or otherwise support and handle the noisemaker 100 during use of the noisemaker 100. It will be appreciated that the number, shape, or size of the handles 220 should not be considered limiting on the current disclosure as it can be contemplated that any number, shape, or size of the handles 220 can be utilized. In one aspect, the handle assembly 214 can be secured to the noisemaker housing 112 via supports 216a,b,c,d connected to the body 218. It will be appreciated that the number of supports 216a,b,c,d should not be considered limiting on the current disclosure as it is contemplated that any number of supports 216 may be utilized.

Figure 3:
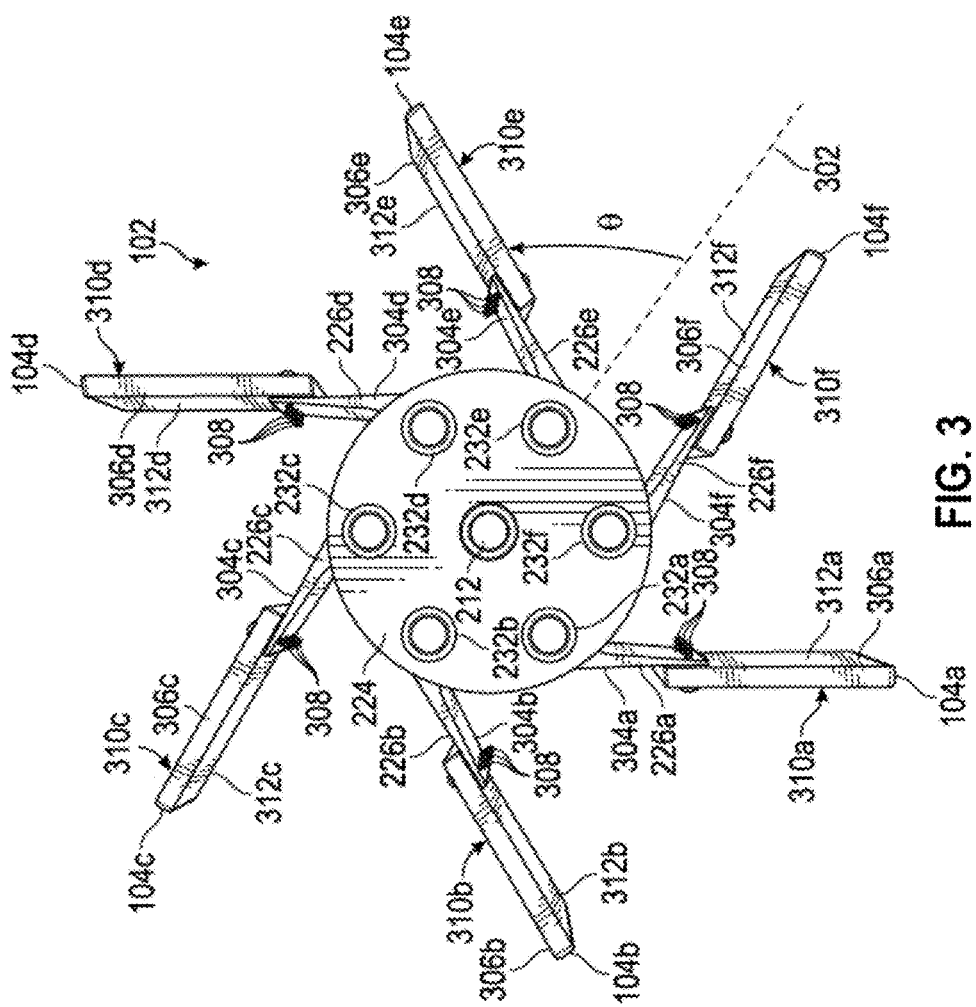
FIG. 3 is a side view of the actuator of FIG. 2.

Referring to FIG. 3, each flap 226a,b,c,d,e,f can comprise a rigid arm 304a,b,c,d,e,f and a flexible arm 306a,b,c,d,e,f connected to the rigid arms 304a,b,c,d,e,f, respectively. In one aspect, the flexible arms 306a,b,c,d,e,f can be connected to the rigid arms 304a,b,c,d,e,f, respectively, through arm connectors 308. The number of arm connectors 308 securing the flexible arms 306a,b,c,d,e,f to the rigid arms 304a,b,c,d,e,f should not be considered limiting on the current disclosure. It is also contemplated that various other types of connections can be utilized in place of the arm connectors 308 to secure the flexible arms 306 to the rigid arms 304, such as those from the group including, but not limited to, welding, various adhesives, press-fit connections, and various other types of connections.

In one aspect, the rigid arms 304a,b,c,d,e,f can be secured to the hub 224 and configured to support the flexible arms 306a,b,c,d,e,f, respectively. The flexible arms 306a,b,c,d,e,f can be constructed from a flexible material with elastic properties compared to the material used to construct rigid arms 304a,b,c,d,e,f. The elastic properties of the flexible arms 306a,b,c,d,e,f can enable flexing or bending of the flexible arms 306a,b,c,d,e,f upon engagement with the vibrating plate 106. In one aspect, at least a portion of the flexible arms 306a,b,c,d,e,f can be configured to engage the vibrating plate 106. The type of material used to construct the flexible arms 306a,b,c,d,e,f can be varied depending on a desired frequency to be generated, a type of node material that the flexible arms 306 can be configured to engage with, or the node or pipe size that the flexible arms 306 can be configured to engage with. In another aspect, each flap 226a,b,c,d,e,f can be constructed from a single type of material As previously described, the flexible arms 306a,b,c,d,e,f can define the tapping tips 104a,b,c,d,e,f, respectively. In one aspect, the noisemaker 100 can be configured such that the tapping tips 104 engage the vibrating plate 106. In a further aspect, the tapping tips 104 can be wear-resistant tips, which can be constructed from various materials depending on the node (e.g. pipe) material, type of signal that the operator wants to generate, and the size of the pipe in which the acoustic signal is to be generated. In one aspect, the tapping tips 104 can be constructed from different structures such as those from the group including, but not limited to, solid pieces of rubber, metal brushes comprising a plurality of strands, and various other structures for engaging the vibrating plate 106. For example and without limitation, a tapping tip 104 configured to generate the acoustic signal in a small diameter metallic pipe can be constructed from a relatively harder material compared to a material used to construct a tapping tip 104 configured to generate the acoustic signal in a plastic pipe. It is contemplated that the tapping tips 104 can be constructed from the same material used to construct the flexible arms 306 or can be constructed from a different material. Depending on the adjustable distance 140 at which the vibrating plate 106 is placed relative to the actuator 102, more than just the tapping tips 104a,b,c,d,e,f of the flaps 226a,b,c,d,e,f may engage the vibrating plate 106.

Referring to FIG. 3, the flexible arms 306a,b,c,d,e,f can define first engagement surfaces 310a,b,c,d,e,f, and second engagement surfaces 312a,b,c,d,e,f, respectively, which can engage the vibrating plate 106. For example and without limitation, at certain adjustable distances 140, first engagement surfaces 310a,b,c,d,e,f can engage the top surface 108 of the vibrating plate 106 and slide over the top surface 108 due to the elastic properties of the flexible arms 306a,b,c, d,e,f as the flaps 226 are rotated. The actuator 102 with the flexible arms 306 can be utilized to generate a brushing contact with the top surface 108 of the vibrating plate 106 because the flaps 226a,b,c,d,e,f respectively, can slide along the top surface 108 of the vibrating plate 106 for a distance as the flaps 226a,b,c,d,e,f are rotated. The distance for which the flaps 226a,b,c,d,e,f remain in contact with the top surface 108 can be adjustable depending on the adjustable distance 140 at which the vibrating plate 106 is positioned relative to the actuator 102.

Figure 4:
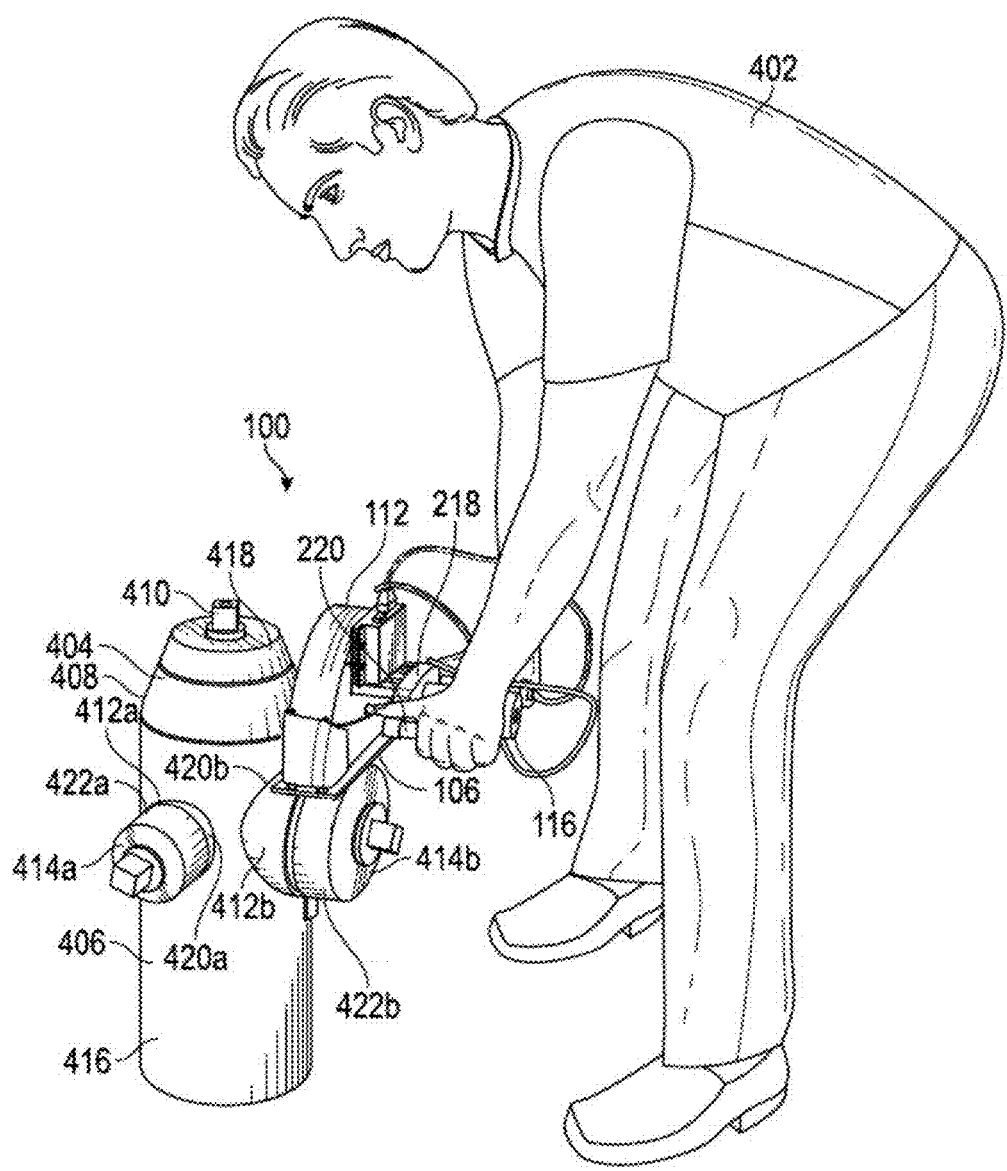
FIG. 4 is a perspective view of the noisemaker of FIG. 2 being used by an operator on a fire hydrant according to one aspect of the current disclosure.

Referring to FIG. 4, the noisemaker 100 can be utilized by an operator 402 on a fire hydrant 404. However, it is contemplated that the noisemaker 100 can be used by the operator 402 to engage other elements or nodes of an infrastructure piping systems. The fire hydrant 404 can be a dry-barrel fire hydrant having a hydrant body 406 and a bonnet 408 connected to a top end of hydrant body 406. A hydrant shoe (not shown) can be connected to a bottom end of the hydrant body 406 and can be connected to a water supply pipe or any other fluid supply pipe. In another aspect, the hydrant 404 can be other types of fire hydrants, such as a wet-barrel fire hydrant, and the disclosure of a dry-barrel fire hydrant should not be considered limiting on the current disclosure.

An operating nut 410 having a threaded connection with a stem (not shown) of the fire hydrant 404 can be mounted on the bonnet 408. The stem can be connected to a main valve (not shown) of the hydrant 404 such that operation of the operating nut 410 can open the main valve to allow water to flow from the water supply pipe to the hydrant body 406 or can close the main valve to discontinue water flow from the water supply pipe to the hydrant body 406. The main valve can be opened and closed by turning the operating nut 410 to actuate the main valve between an open position and a closed position. In one aspect, the fire hydrant 404 can comprise nozzles 412a,b which can provide access to an interior of the hydrant body 406. In another aspect, the fire hydrant 404 can comprise nozzle caps 414a,b to cover the nozzles 412a,b when the fire hydrant 404 is not being utilized or when access to the interior of the hydrant body 406 is not needed. As shown in FIG. 4, the hydrant body 406 can comprise an exterior surface 416, the bonnet 408 can comprise an exterior surface 418, the nozzles 412,a,b can comprise exterior surfaces 420a,b, respectively, and the nozzle caps 414a,b, can comprise exterior surfaces 422a,b, respectively.

In one aspect, the noisemaker 100 can be positioned by the operator 402 such that the bottom surface 110 of the vibrating plate 106 is in contact with the exterior surfaces 420b,422b. However, it is contemplated that the operator 402 can position the noisemaker 100 such that the bottom surface 110 of the vibrating plate 106 is in contact with any of the exterior surfaces of the hydrant 404. In a further aspect, the noisemaker 100 can be positioned on the fire hydrant 404 such that the vibrating plate 106 is positioned between the flaps 226 and the exterior surfaces 420b,422b of the fire hydrant 404. The operator 402 can utilize the noisemaker 100 to generate an acoustic signal by causing the actuator 102 to engage the vibrating plate 106. The frequency at which the flaps 226 impact the vibrating plate 106 can be proportional to the rotational speed of the motor 116. For a given rotational speed, the fire hydrant 404 will be excited with a frequency based on the following equation:

$$f = \Omega \cdot N$$

where N is the number of flaps and $\Omega$ is the rotational speed (in rotation per sec).

In another aspect, the operator 402 can adjust the distance at which the vibrating plate 106 is positioned relative to the actuator 102. As previously described, adjusting the adjustable distance 140 can adjust the amount of acoustic energy transferred from the actuator 102 to the fire hydrant 404 via the vibrating plate 106, the impact force of the flaps 226 engaging the vibrating plate 106, and a duration of the impact force of the flaps 226 engaging the vibrating plate 106. In one non-limiting example, a relatively small distance between the vibrating plate 106 and the actuator 102 can force the flexible arms 306a,b,c,d,e,f to flex more as greater portions of the tapping tips 104a,b,c,d,e,f and the first engagement surfaces 310a,b,c,d,e,f, respectively, engage the vibrating plate 106 for a relatively longer duration. An increased amount of the flexible arms 306a,b,c,d,e,f engaging the vibrating plate 106 can increase the impact force applied to the vibrating plate 106 and the amount of acoustic energy transferred to the fire hydrant 404. In another non-limiting example, a relatively large distance between the vibrating plate 106 and the actuator 102 can force the flexible arms 306a,b,c,d,e,f to flex relatively less as less of the tapping tips 104a,b,c,d,e,f and the first engagement surfaces 310a,b,c,d,e,f, respectively, engage the vibrating plate 106 for a relatively shorter duration. A decreased amount of the flexible arms 306a,b,c,d,e,f engaging the vibrating plate 106 can decrease the impact force applied to the vibrating plate 106 and decreases the amount of acoustic energy transferred to the fire hydrant 404. In one aspect, after the operator 402 has positioned the vibrating plate 106 at a desired distance from the actuator 102, the vibrating plate 106 can maintain that desired distance from the actuator 102 while the noisemaker 100 is being utilized to generate the acoustic signal.

An objective of the noisemaker 100 can be to inject sound into a fluid-filled pipe in order to determine the propagation speed of the acoustic waves in the fluid-pipe system. To estimate the propagation speed, the sound can be sensed by multiple sensors, such as at least two sensors, placed at various locations along the pipe. Various sensing technologies can be used for the sensors, including but not limited to piezoelectric accelerometers placed on a pipe surface, hydrophones placed in the water column, or electromagnetic sensors to measure the radial velocity of the pipe wall. Based on the distances between sensors, the propagation speed of acoustic waves and the propagation delay of the signal observed at multiple locations along the pipe can be determined.

FIGS. 5A and 5B show a block diagram of another example of a noisemaker 500. As shown in FIGS. 5A and 5B, the noisemaker 500 can comprise an actuator 502 and the vibrating plate 106. The noisemaker 500 also can comprise the noisemaker housing 112. Although not shown, in various aspects the noisemaker 500 can comprise the motor 116, the motor control 118, the excitation control 122, and the user interface 124.

Referring to FIGS. 5A and 5B, the vibrating plate 106 can be positioned at the adjustable distance 140 such that the top surface 108 of the vibrating plate 106 contacts a bottom end 506 of the noisemaker housing 112. However, similar to the noisemaker 100, the vibrating plate 106 can positionable at the adjustable distance 140 relative to the actuator 502 such that the top surface 108 may or may not be in contact with the bottom end 506. In another aspect, the distance between the actuator 502 and the vibrating plate 106 can be non-adjustable and thereby fixed, and the vibrating plate 106 can be at the non-adjustable position with the top surface 108 in contact with the bottom end 506 or with the top surface 108 not in contact with the bottom end 506.

The actuator 502 can be configured to engage the vibrating plate 106 to generate the acoustic signal. In various aspects, the actuator 502 can comprise a tapping tip 504, which can be configured to engage the vibrating plate 106. Similar to the tapping tips 104, the tapping tip 504 can be constructed from various materials depending on the node (e.g. pipe) material, type of signal that the operator wants to generate, and the size of the pipe in which the acoustic signal can be to be generated. FIG. 5A shows the tapping tip 504 in a disengaged position and FIG. 5B shows the tapping tip 504 in an engaged position. As shown in FIG. 5A, in the disengaged position, the tapping tip 504 can be spaced apart from the vibrating plate 106. In one aspect, in the disengaged position, a contact surface 508 of the tapping tip 504 can be spaced apart from the top surface 108 of the vibrating plate 106. As shown in FIG. 5B, in the engaged position, the tapping tip 504 contacts the vibrating plate 106. In another aspect, in the engaged position, the contact surface 508 of the tapping tip 504 can be in contact with the top surface 108 of the vibrating plate 106.

The actuator 502 can comprise a mobile housing 510 positioned within the noisemaker cavity 202. As shown in FIGS. 5A and 5B, the mobile housing 510 can comprise an inner surface 512 and an outer surface 514. In one aspect, the actuator 502 can comprise a tapping rod 530 secured to and extending from the outer surface 514 of the mobile housing 510 at a bottom end 524. In another aspect, the tapping tip 504 can be secured to the tapping rod 530. The tapping tip 504 and the tapping rod 530 can be constructed from the same type of material or from different types of materials. In one non-limiting example, the tapping tip 504 can be constructed from a flexible material with elastic properties and the tapping rod 530 can be constructed from a rigid material. In another non-limiting example, the tapping tip 504 can be a component of the tapping rod 530 and the tapping tip 503 and tapping rod 530 can be continuously formed. When the distance between the actuator 502 and the vibrating plate 106 is non-adjustable, the material of the tapping tip 504 can optionally be removable and changeable to control the characteristics of the acoustic signal generated by the tapping tip 504 contacting the vibrating plate 106.

In another aspect, the inner surface 512 of the mobile housing 510 can define a mobile housing cavity 516. As shown in FIGS. 5A and 5B, the actuator 502 can comprise a rotating cam 518. In one aspect, the rotating cam 518 can be mounted on the drive shaft 212 connected to the motor 116. The rotating cam 518 can be configured to rotate as indicated by reference arrow A such that the rotating cam 518 selectively engages and disengages the mobile housing 510. In one aspect, the rotating cam 518 can be dimensioned or positioned such that the rotating cam 518 engages the mobile housing 510 at one of a top end 522 or the bottom end 524 of the mobile housing 510 to move the mobile housing 510 between the engaged position and the disengaged position. In a further aspect, the rotating cam 518 can be configured to engage the top end 522 of the mobile housing 510. It will be appreciated that the shape of the rotating cam 518 should not be considered limiting on the current disclosure as it is contemplated that other geometric shapes of the rotating cam 518 can be present.

In the aspect where the rotating cam 518 can be configured to engage the top end 522 of the mobile housing 510 as shown in FIG. 5A, in the disengaged position, an outer surface 520 of the rotating cam 518 can engage and be in contact with the inner surface 512 of the mobile housing 510 at the top end 522. In another aspect as shown in FIG. 5B, in the engaged position, the outer surface 520 of the rotating cam 518 can be spaced apart and not in contact with the inner surface 512 of the mobile housing 510.

In another aspect where the rotating cam 518 can be configured to engage the inner surface 512 at the bottom end 524 of the mobile housing 510, in the engaged position, the outer surface 520 of the rotating cam 518 can engage the inner surface 512 of the mobile housing 510 at the bottom end 524. In this aspect, in the disengaged position, the outer surface 520 of the rotating cam 518 can be spaced apart and not in contact with the inner surface 512 of the mobile housing 510.

In yet another aspect, the noisemaker 500 can comprise springs 526a,b, which can secure the mobile housing 510 to the noisemaker housing 112. It will be appreciated that the number of springs 526 should not be considered limiting on the current disclosure. In one aspect, the springs 526a,b can be secured to the outer surface 514 of the mobile housing 510 at the top end 522 and to an inner surface 532 of the noisemaker housing 112 at a top end 528 of the noisemaker housing 112. The springs 526a,b can be moved between a compressed position (shown in FIG. 5A) and an extended position (shown in FIG. 5B) to aid in moving the tapping tip 504 between the disengaged position and the engaged position. In one aspect, the springs 526a,b can be adjustable to adjust a spring force generated by the springs 526a,b moving from the compressed position to the extended position. In another aspect, the spring force can be adjusted by using a different number of springs 526, by using a different type of spring 526, or any combination thereof. Adjusting the spring force can adjust an impact force of the tapping tip 504 engaging the vibrating plate 106. In another aspect, the impact force generated can be adjustable by adjustably positioning the vibrating plate 106 relative to the actuator 502. In various other aspects, the springs 526a,b can be omitted and the mobile housing 510 may not be secured to the noisemaker housing 112.

Figure 6A:
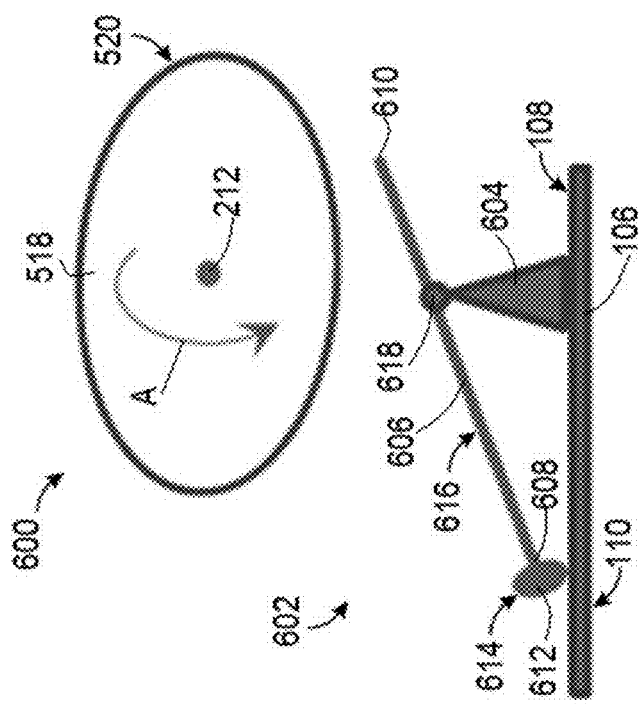
FIG. 6A is a block diagram of a noisemaker comprising an actuator and a vibrating plate with the actuator in a disengaged position in accordance with one aspect of the current disclosure.
Figure 6B:
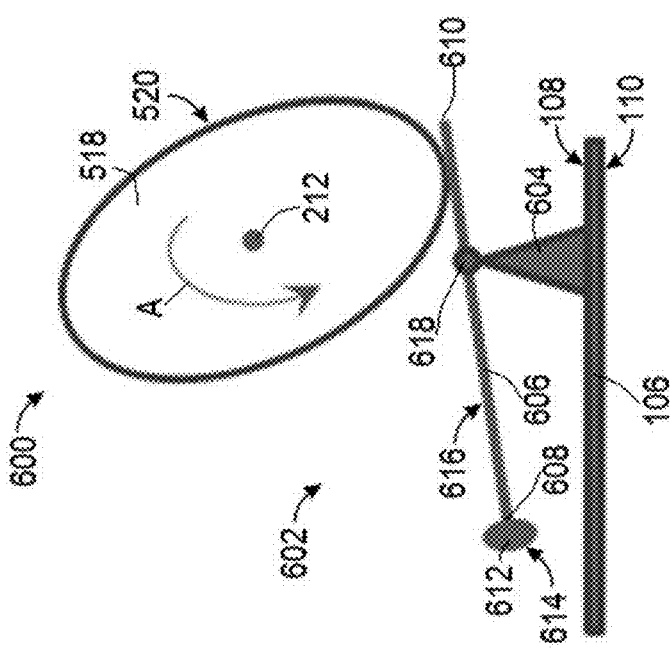
FIG. 6B is a block diagram of the noisemaker of FIG. 6A with the actuator and the vibrating plate in an engaged position in accordance with one aspect of the current disclosure.

FIGS. 6A and 6B show a block diagram of another example of a noisemaker 600. The noisemaker 600 can comprise an actuator 602 and the vibrating plate 106. Although not shown, the noisemaker 600 can comprise the motor 116, the motor control 118, the excitation control 122, the user interface 124, and the noisemaker housing 112 defining the noisemaker cavity 202.

As shown in FIGS. 6A and 6B, similar to the actuator 502, the actuator 602 can comprise the rotating cam 518 mounted on the drive shaft 212. In another aspect, the actuator 602 can comprise a fulcrum 604 secured to the top surface 108 of the vibrating plate 106. The fulcrum 604 can be configured to pivotably support a pivoting rod 606. The pivoting rod 606 can comprise a first end 608 and a second end 610. In another aspect, a tapping tip 612, which can be functionally similar to the tapping tips 104,504, can be secured to the first end 608 of the pivoting rod 606; however, it is contemplated that the tapping tip 612 and the tapping rod 606 can also be continuously formed. The tapping tip 612 can be configured to engage the vibrating plate 106 to generate the acoustic signal. As shown in FIGS. 6A and 6B, the pivoting rod 606 can define an outer surface 616 extending between the first end 608 and the second end 610.

The rotating cam 518 can be configured to engage the pivoting rod 606 and move the tapping tip 612 between a disengaged position (shown in FIG. 6A) and an engaged position (shown in FIG. 6B). As shown in FIG. 6A, in the disengaged position, a contact surface 614 of the tapping tip 612 can be spaced apart from the vibrating plate 106. In the disengaged position, the outer surface 520 of the rotating cam 518 can engage and be in contact with the outer surface 616 of the pivoting rod 606 between a pivoting point 618, which can be where the fulcrum 604 supports the pivoting rod 606, and the second end 610 of the pivoting rod 606. As shown in FIG. 6B, in the engaged position, the contact surface 614 of the tapping tip 612 can be in contact with the top surface 108 of the vibrating plate 106. In the engaged position, the rotating cam 518 can not be engaged with the pivoting rod 606.

An impact force generated by the tapping tip 612 engaging the vibrating plate 106 can be related to a mass of the tapping tip 612. In various aspects, the impact force can be adjustable by adjustably positioning the vibrating plate 106 relative to the rotating cam 518. For example and without limitation, positioning the vibrating plate 106 relatively close to the rotating cam 518 can generate a relatively greater impact force compared to positioning the vibrating plate 106 at a relatively spaced apart distance. In another aspect, the impact force can be adjustable by adjusting a height of the fulcrum 604, which can be a distance from the top surface 108 of the vibrating plate 106 to the pivoting point 618. In yet another aspect, the impact force can be adjustable by adjusting the pivot point 618, or where the pivoting rod 606 can be connected to the fulcrum 604, along the pivoting rod 606 between the ends 608,610. In another aspect, the actuator 602 can comprise springs to aid in moving the tapping tip 612 between the engaged position and the disengaged position.

A method of generating sound in an infrastructure system is also disclosed. Although reference will be made to the noisemaker 100, the following description can be equally applicable to the noisemakers 500, 600.

The method can comprise placing the bottom surface 110 of the vibrating plate 106 of the noisemaker 100 in contact with an exterior surface of a node of the infrastructure system, such as a hydrant, a pipe element, a valve housing, or various other locations within the infrastructure system. The method can comprise generating an acoustic signal with the noisemaker 100. In one aspect, generating the acoustic signal can comprise activating the motor 116 configured to drive the actuator 102. In this aspect, activating the motor 116 can comprise interacting with the user interface 124 and selecting or inputting a desired frequency at which the actuator 102 engages the vibrating plate 106. In this aspect, the frequency at which the actuator 102 engages the vibrating plate 106 can be proportional to the rotational speed of the motor 116. In another aspect, activating the motor 116 can comprise providing an excitation sequence for the actuator 102. In this aspect, providing the excitation sequence can comprise engaging the user interface 124 to select an excitation sequence stored by the excitation control 122.

The method can further comprise adjusting the distance between the vibrating plate 106 and the actuator 102. In one aspect, adjusting the distance between the vibrating plate 106 and the actuator 102 adjusts the impact force of the actuator 102 with the vibrating plate 106. In another aspect, the method can comprise adjusting the frequency at which the actuator 102 engages the vibrating plate 106. In this aspect, adjusting the frequency adjusts the frequency at which the tapping tips 104 of the actuator 102 engage the top surface 108 of the vibrating plate 106 and the speed at which the hub 224 and flaps 226 are rotated by the motor 116 via the drive shaft 212.

Unlike the noisemaker 100, which produces a brushing contact between the flaps 226a,b,c,d,e,f and the top surface 108 of the vibrating plate 106, the noisemakers 500, 600 can be utilized to produce an impact contact with the top surface 108 of the vibrating plate 106. As described above, in the brushing contact, the position of the tapping tips 104a,b,c,d,e,f on the top surface 108 of the vibrating plate 106 can change while the tapping tips 104a,b,c,d,e,f engage the top surface 108, respectively. In the impact contact, the position of the tapping tips 504,612 on the top surface 108 can remain the same while the tapping tips 504,612 engage the top surface 108, respectively.

It should be emphasized that the above-described aspects are merely possible examples of implementations, merely set forth for a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims which follow, they are used only in a generic and descriptive sense, and not for the purposes of limiting the described invention, nor the claims which follow.

That which is claimed is:

1. A noisemaker system comprising:
   a node of an infrastructure system; and
   a noisemaker comprising:
      a vibrating plate comprising a top surface and a bottom surface, the bottom surface of the vibrating plate in contact with an exterior surface of the node;
      an actuator configured to engage the top surface of the vibrating plate and generate an acoustic signal;
      a motor configured to drive the actuator to engage the top surface of the vibrating plate;
      a user interface;
      an excitation control communicatively coupled to the user interface, wherein a user may utilize the user interface to select an excitation sequence of the excitation control for the actuator; and
      a motor control communicatively coupled to the excitation control, wherein the motor control is a frequency control communicatively coupled to the motor.

2. The noisemaker system of claim 1, wherein the noisemaker further comprises a noisemaker housing defining a noisemaker cavity, wherein the actuator is positioned at least partially within the noisemaker cavity.

3. The noisemaker system of claim 1, wherein the vibrating plate is positioned at an adjustable distance from the actuator.

4. The noisemaker system of claim 3 wherein a connector secures the vibrating plate to a noisemaker housing of the noisemaker, and wherein the connector is configured to adjustably position the vibrating plate at the adjustable distance from the actuator.

5. The noisemaker system of claim 1, wherein the actuator comprises a hub and a flap connected to the hub and extending outwards from the hub, wherein the noisemaker further comprises a motor configured to rotate the hub and the flap, and wherein the flap is configured to contact the top surface of the vibrating plate and generate the acoustic signal.

6. The noisemaker system of claim 5, wherein the flap comprises a flexible arm secured to a rigid arm, wherein the rigid arm is connected to the hub, and wherein at least a portion of the flexible arm is configured to contact the top surface of the vibrating plate and generate the acoustic signal.

7. The noisemaker system of claim 1, wherein the noisemaker further comprises a noisemaker housing defining a noisemaker cavity, and wherein the actuator comprises:
a mobile housing positioned within the noisemaker cavity, the mobile housing defining a mobile housing cavity;
a spring securing the mobile housing to the noisemaker housing within the noisemaker cavity;
a tapping rod secured to the mobile housing and configured to contact the top surface of the vibrating plate and generate the acoustic signal; and
a rotating cam positioned within the mobile housing cavity and configured to adjustably position the mobile housing and the tapping rod within the noisemaker cavity.

8. The noisemaker system of claim 7, wherein the tapping rod contacts the top surface of the vibrating plate in an engaged position, wherein the rotating cam is configured to adjustably position the tapping rod between the engaged position and a disengaged position, and wherein in the disengaged position, the tapping rod is not in contact with the top surface of the vibrating plate.

9. The noisemaker system of claim 1, wherein the actuator comprises:
a fulcrum secured to the top surface of the vibrating plate;
a pivoting rod supported by the fulcrum, the pivoting rod comprising a first end and a second end, the first end comprising a tapping tip configured to contact the top surface of the vibrating plate and generate the acoustic signal; and
a rotating cam configured to contact the second end of the pivoting rod.

10. A noisemaker comprising:
a noisemaker housing defining a noisemaker cavity and a housing opening;
a vibrating plate secured to the noisemaker and positioned proximate to the housing opening, the vibrating plate comprising a top surface and a bottom surface; and
an actuator positioned at least partially within the noisemaker cavity, the actuator configured to engage the top surface of the vibrating plate and generate an acoustic signal;
wherein the actuator comprises:
a mobile housing positioned within the noisemaker cavity, the mobile housing defining a mobile housing cavity;
a spring securing the mobile housing to the noisemaker housing within the noisemaker cavity;
a tapping rod secured to the mobile housing and configured to contact the top surface of the vibrating plate and generate the acoustic signal; and
a rotating cam positioned within the mobile housing cavity and configured to adjustably position the mobile housing and the tapping rod within the noisemaker cavity.

11. A method of generating sound in an infrastructure system, the method comprising:
placing a bottom surface of a vibrating plate of a noisemaker in contact with an exterior surface of a pipe element of the infrastructure system;
generating an acoustic signal by contacting an actuator of the noisemaker with a top surface of the vibrating plate; and
adjusting a frequency at which the actuator contacts the top surface of the vibrating plate;
wherein the actuator comprises a hub and a flap connected to the hub and extending outwards from the hub, wherein generating the acoustic signal comprises rotating the hub and the flap, and wherein adjusting the frequency at which the actuator contacts the top surface of the vibrating plate comprises adjusting a speed at which the hub and the flap are rotated.

12. The method of claim 11, further comprising adjusting a distance between the vibrating plate and the actuator.

13. The method of claim 11, wherein generating the acoustic signal further comprises one of producing an impact contact with the top surface of the vibrating plate by the actuator and producing a brushing contact with the top surface of the vibrating plate by the actuator.

14. A noisemaker system comprising:
a node of an infrastructure system; and
a noisemaker comprising:
a noisemaker housing defining a noisemaker cavity;
a vibrating plate comprising a top surface and a bottom surface, the bottom surface of the vibrating plate in contact with an exterior surface of the node; and
an actuator configured to engage the top surface of the vibrating plate and generate an acoustic signal, the actuator comprising:
a mobile housing positioned within the noisemaker cavity, the mobile housing defining a mobile housing cavity;
a spring securing the mobile housing to the noisemaker housing within the noisemaker cavity;
a tapping rod secured to the mobile housing and configured to contact the top surface of the vibrating plate and generate the acoustic signal; and
a rotating cam positioned within the mobile housing cavity and configured to adjustably position the mobile housing and the tapping rod within the noisemaker cavity.

15. The noisemaker system of claim 14, wherein the tapping rod contacts the top surface of the vibrating plate in an engaged position, wherein the rotating cam is configured to adjustably position the tapping rod between the engaged position and a disengaged position, and wherein in the disengaged position, the tapping rod is not in contact with the top surface of the vibrating plate.

16. A noisemaker system comprising:
a node of an infrastructure system; and
a noisemaker comprising
a vibrating plate comprising a top surface and a bottom surface, the bottom surface of the vibrating plate in contact with an exterior surface of the node; and an actuator configured to engage the top surface of the vibrating plate and generate an acoustic signal, the actuator comprising:
- a fulcrum secured to the top surface of the vibrating plate;
- a pivoting rod supported by the fulcrum, the pivoting rod comprising a first end and a second end, the first end comprising a tapping tip configured to contact the top surface of the vibrating plate and generate the acoustic signal; and
- a rotating cam configured to contact the second end of the pivoting rod.

17. A noisemaker comprising:

a noisemaker housing defining a noisemaker cavity and a housing opening;

a vibrating plate secured to the noisemaker and positioned proximate to the housing opening, the vibrating plate comprising a top surface and a bottom surface; and an actuator positioned at least partially within the noisemaker cavity, the actuator configured to engage the top surface of the vibrating plate and generate an acoustic signal, the actuator comprising:
- a fulcrum secured to the top surface of the vibrating plate;
- a pivoting rod supported by the fulcrum, the pivoting rod comprising a first end and a second end, the first end comprising a tapping tip configured to contact the top surface of the vibrating plate and generate the acoustic signal; and
- a rotating cam configured to contact the second end of the pivoting rod.

* * * * *